United States Patent
Manente

(10) Patent No.: US 6,293,919 B1
(45) Date of Patent: Sep. 25, 2001

(54) HAND BRACE

(76) Inventor: Gabriele Manente, Via Colle di Giorgio, 3, Castellalto (TE) (IT)

( * ) Notice: Subject to any disclaimer, the term of this patent is extended or adjusted under 35 U.S.C. 154(b) by 0 days.

(21) Appl. No.: 09/371,198

(22) Filed: Aug. 10, 1999

(30) Foreign Application Priority Data

Sep. 7, 1998 (IT) .............................. TE98A0006

(51) Int. Cl.$^7$ .............................. A61F 5/00; A61F 13/00; A61F 5/37; A41D 19/08
(52) U.S. Cl. ................ 602/21; 602/64; 602/22; 128/879; 2/163
(58) Field of Search .................... 602/20–22, 60–64, 602/5–6; 2/16, 20, 21, 163, 161.1, 161.2, 161.5, 161.6; 473/59, 61, 62; 5/630, 632, 634, 646, 647; 482/44, 47–48; 128/845–846, 878–880

(56) References Cited

U.S. PATENT DOCUMENTS

| | | | | |
|---|---|---|---|---|
| 2,763,864 | * | 9/1956 | Conrad, Jr. ................................. | 2/16 |
| 3,049,717 | * | 8/1962 | Meyer ........................................ | 2/16 |
| 3,224,012 | * | 12/1965 | Hamm .................................... | 2/161.2 |
| 3,595,575 | * | 7/1971 | Gooch ...................................... | 1/162 |
| 5,005,824 | * | 4/1991 | Eichel ..................................... | 272/67 |
| 5,367,712 | * | 11/1994 | Smith et al. ............................. | 2/162 |
| 5,413,553 | * | 5/1995 | Downes .................................. | 602/21 |
| 5,527,040 | * | 6/1996 | Stanley et al. ........................ | 473/213 |
| 5,708,981 | * | 1/1998 | Tilton .................................. | 602/21 X |
| 5,733,249 | * | 3/1998 | Katzin et al. ....................... | 602/64 X |
| 5,839,124 | * | 11/1998 | Tilton ...................................... | 2/170 |
| 5,865,783 | * | 2/1999 | Klimoski ............................... | 602/64 |
| 6,106,492 | * | 8/2000 | Darcey ..................................... | 602/8 |

FOREIGN PATENT DOCUMENTS

| | | | | |
|---|---|---|---|---|
| 112684 | * | 1/1918 | (GB) ..................................... | 602/21 |
| 222269 | * | 10/1924 | (GB) ..................................... | 602/21 |

OTHER PUBLICATIONS

Malick, "Manual on Static Hand Splinting," 1972.*

* cited by examiner

Primary Examiner—Denise Pothier
(74) Attorney, Agent, or Firm—Leonard Bloom

(57) ABSTRACT

The present invention relates to a hand brace comprising a bandage capable of embracing the external regions of the distal ends of the metacarpal bones of the II° and V° finger, which incorporates a dorsal support, composed of a coated and internally padded plate made of semi-rigid material, fixed to a soft cushion shaped like a prism with cuneiform cross-section, which can be situated in intermediate position between the II° and the V° finger.

6 Claims, 2 Drawing Sheets

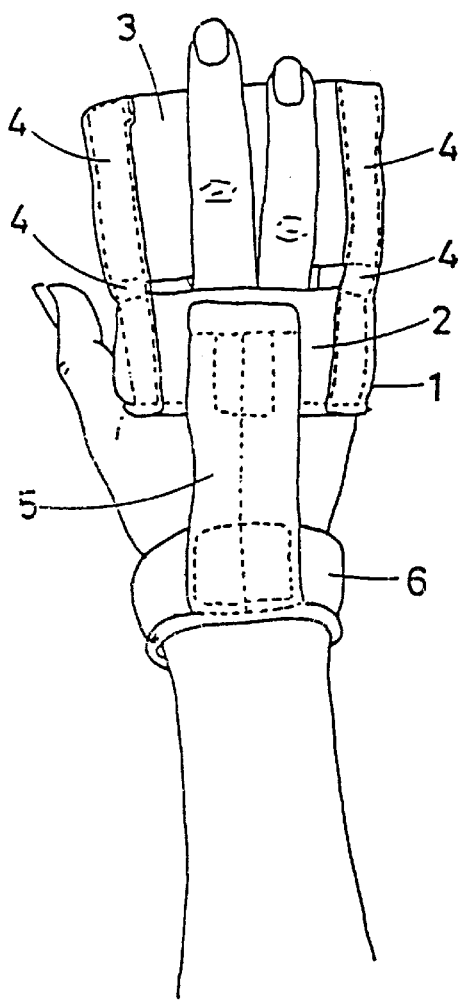
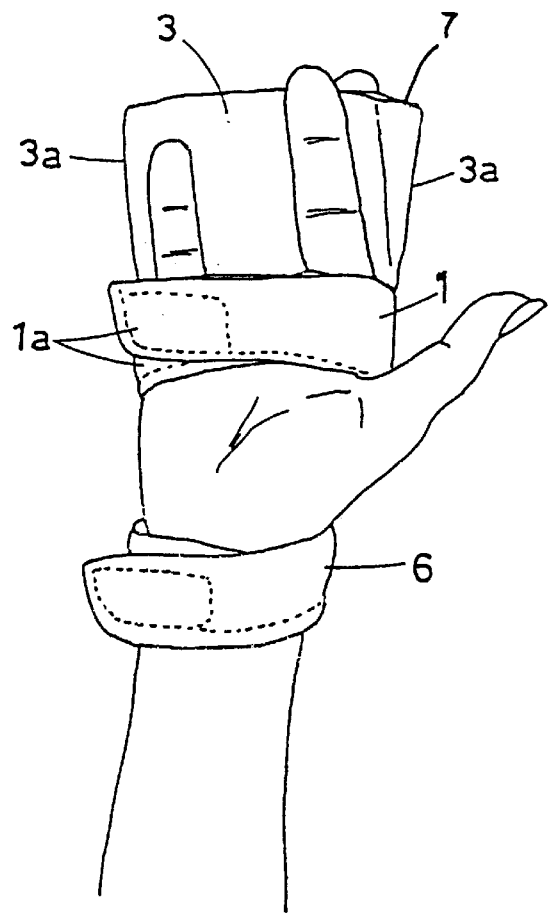
FIG. 1
FIG. 2

HAND BRACE

CROSS REFERENCES TO RELATED APPLICATIONS not applicable.

STATEMENT REGARDING FEDERALLY SPONSORED RESEARCH OR DEVELOPMENT not applicable.

BACKGROUND OF THE INVENTION

1. Field of the Invention

The present invention relates to a hand brace, designed for the conservative treatment of the carpal tunnel syndrome (CTS).

This brace can be defined as dynamic, because it not only has a simple protective and supporting action, as explained in detail below.

The carpal tunnel syndrome (CTS) affects 9.2% of women and 0.6% of men (Journal of epidemiology, 1992) and consists in the neuropathy of the median nerve during the passage through the carpal tunnel.

It is often associated with repeated professional microtrauma, more rarely with amyloid infiltration of the transverse carpal ligament, thickening of the connective tissue in rheumatoid arthritis, hypothyroidism, etc. However, in a large number of cases the CTS is idiopathic.

The main symptoms are represented by paresthesia of the hand (first 3–4 fingers) and pain of the upper limb, up to the shoulder.

Initially, the symptoms only occur during the night or in the morning after waking up. Successively, they start occurring during the day, especially in association with an intense use of the hand.

At a later stage persistent sensory deficiencies and muscular hypotrophy of the thenar eminence occur.

The treatment can be either surgical or conservative.

The surgical treatment is generally reserved to those cases with evident significant neuropathy or to those cases that do not respond to the existing conservative treatments. Generally, it consists in the resection of the transverse carpal ligament.

The conservative treatment is reserved to those cases without neuropathy or with modest neuropathy at the neurophysiological examination, in particular if the symptomatology is not progressive or significant, and in those cases in which the surgical treatment has some counterindications.

2. Description of the Related Art

Generally, the conservative treatment is scarcely successful and represented by physical therapy (ultrasounds, laser, galvanic trays, ionophoresis, etc.), braces or splints, which-with different shapes-hold the wrist articulation, with no action on fingers or metacarpal heads.

The currently existing braces that affect fingers and metacarpal heads completely differ from the brace according to the present invention and are not capable of having the same functions as the brace according to the present invention.

The brace according to the present invention is based on physiopathological principles and aspects of the CTS that are unknown in the existing literature. The brace according to the present invention comprises a bandage capable of embracing the external regions of the distal metacarpal ends of the II° (index) and V° (little finger) fingers, which incorporates a dorsal support, composed of a coated, internally padded plate made of semi-rigid material. The bandage supports a soft cushion shaped like a prism with cuneiform cross-section, which is capable of being situated in intermediate position between the II° and the V° finger, on one side, and the III° (middle finger) and the IV° (ring finger) finger on the other side, when the brace is worn. More exactly, the II° and the V° finger are located in internal position and the III° and IV° finger in external position with respect to the cushion.

In a preferred embodiment the brace also includes a wrist band connected to the dorsal support incorporated in the bandage with a longitudinal strap.

BRIEF DESCRIPTION OF SEVERAL VIEWS OF THE DRAWINGS

For major clarity the description of the brace according to the invention continues with reference to the enclosed drawings which are intended for purposes of illustration and not in a limiting sense whereby:

FIG. 1 shows the back of a right hand wearing the brace according to the present invention;

FIG. 2 shows the palm of a right hand wearing the brace according to the present invention.

DETAILED DESCRIPTION OF THE INVENTION

Figure 4:
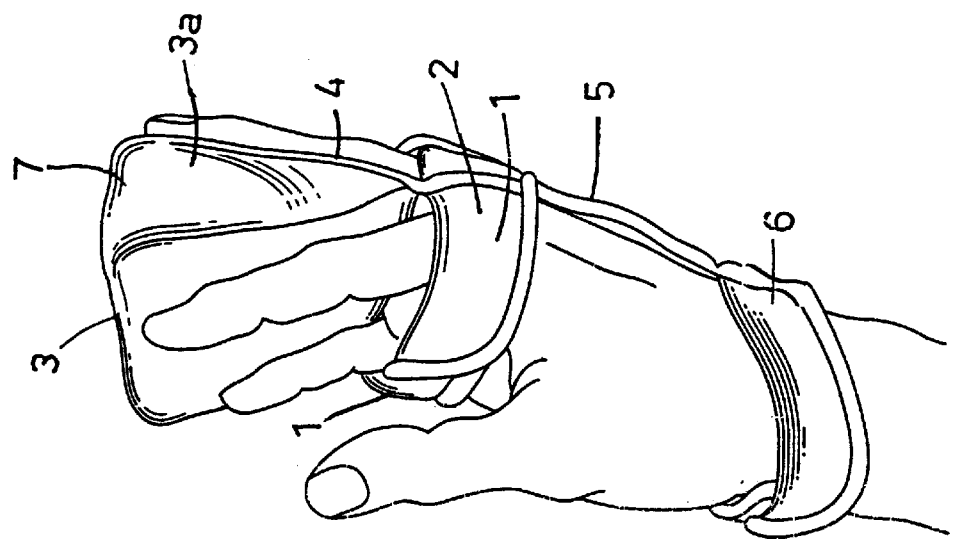
FIG. 4 is a perspective view showing the back of the hand on which is mounted the hand brace of the present invention showing the cuneiform cross section.
Figure 3:
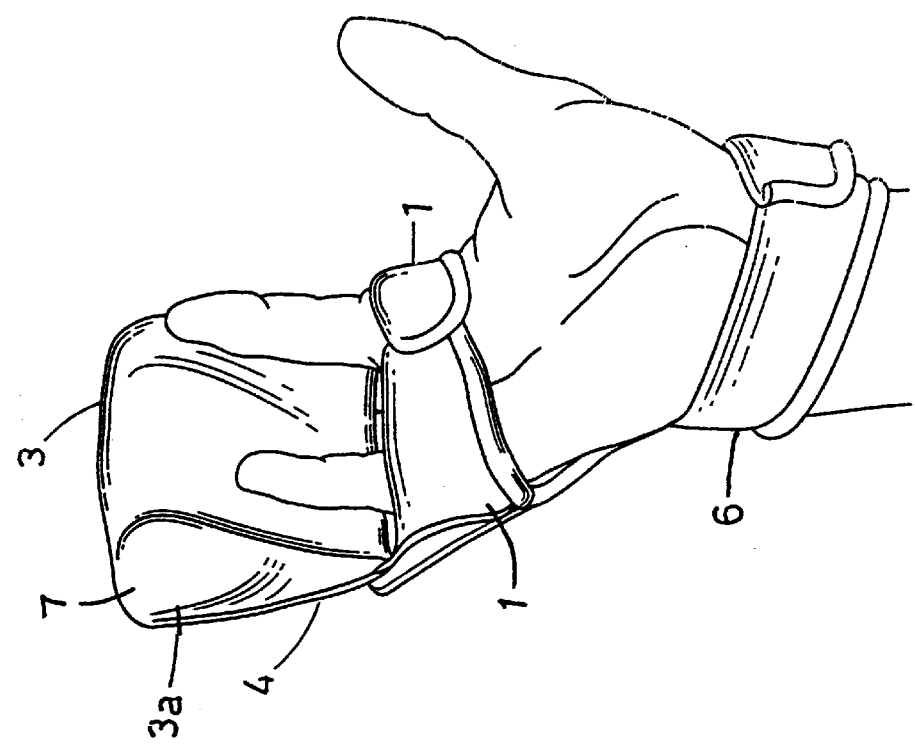
FIG. 3 is a perspective view showing the palm of the hand on which is mounted the hand brace of the present invention showing the cuneiform cross section.

With reference to the above figures, the hand brace according to the present invention comprises a bandage (1) capable of embracing the external regions of the distal ends of the metacarpal bones of the II° (index) and V° (little finger) finger, which incorporates a dorsal support (2), composed of a coated and internally padded plate made with semi-rigid material.

A cushion (3) is fixed to the dorsal support (2), made with soft material and shaped like a prism with cuneiform cross-section, having two faces and a base (7) therebetween which is capable of being situated in intermediate position between the II° and the V° finger, on one side, and the III° (middle finger) and the IV° (ring finger) finger on the other side, when the hand brace is worn.

If the bandage (1) is inelastic, the two ends can be connected by means of appropriate fixing adjustable means. In the hand brace model shown in the enclosed figures, the two ends of the bandage (1) can be placed one on top of the other (1a) and connected with a Velcro layer.

BRIEF SUMMARY OF INVENTION

According to an alternative constructive version—which is not illustrated in the enclosed figures—the bandage can be elastic with annular structure. The bandage (1) allows to apply a force at the level of the external regions of the distal ends of the II° and V° metacarpal bones, by tightening them as necessary, in the case of inelastic bandage, or as provided, in the case of an elastic annular bandage.

The bandage must be tightened enough so as to push the II° and V° metacarpal heads closer to each other, until they are partially overlapped with the III° and IV° heads, respectively, thus obstructing the II° and IV° interdigital space at the level of the first phalanx.

In the case of inelastic bandage the user can adjust the applied force, while in the case of elastic annular bandage the force is determined according to the size and the degree of elastic resistance of the bandage: the user simply inserts the hand brace on his fingers and positions the bandage at the level of the metacarpal heads.

The points of the bandage (1) located on the external regions of the II° and V° metacarpal heads (where the force for the grip is applied) are padded with soft fabric and shaped so that the grip is more comfortable and stable. The cushion (3) is made of various soft materials, such as sponge cloth or fabric, or other substance or material which is soft and comfortable in contact with the fingers.

When the hand brace is worn, the cushion (3) is located between the II° and the V° finger, which assume a fore position (towards the palm), and the III° and IV° finger, which assume a rear position (towards the back) with respect to the cushion.

The III° and IV° finger not only are separated from the II° and V° finger, but also maintained in extended position.

In the preferred embodiment as illustrated in FIGS. 1 and 2 the cushion (3) is connected to the dorsal support (2) by means of a pair of fabric strips (4), which are sewn to the two sides (3a) of the cushion (3) and to the two external sides of the dorsal support (2).

The strips (4) can contain an internal core made up of semi-rigid splints with a certain degree of elastic properties.

In this way, the basic tension and the return elastic tension (following to the forced flexion) of the splints respectively cause the conservation and the return of the extension position of those fingers located in rear position with respect to the cushion.

The hand brace according to the present invention can be provided with a band connected to the dorsal support (2) incorporated into the bandage (1) by means of a longitudinal strap (5), located on the back of the hand and provided with means for easy, adjustable fixing to the wrist band (6) and the support (2).

The wrist band (6) is padded and can be either of elastic annular or open type, provided with adjustable closing means, such as Velcro.

The wrist band (6) with the strap (5) is designed to prevent the hand brace from accidentally slipping off from the fingers.

The strap (5) is externally sewn to the back of the wrist band (6), while the strap (5) can be fixed to the support (2) by means of permanent means, such as stitching, or with movable adjustable means, such as buttons or Velcro inserts.

The strap (5) and the wrist band (6) can be provided with a semi-rigid core, in order to limit the flexor-extensor movements of the wrist, thus favoring the neutral position of the hand.

In particular, the strap (5) can be fixed in a suitable position so as to adjust the ulnar and anteroposterior deviation angle of the hand.

In conclusion, the hand brace simultaneously tightens (either in an adjustable or defined way) the distal metacarpal heads of the II° and V° finger and maintains the III° and IV° finger in extended position. Moreover, the use of the wrist band (6) and the strap (5) avoids the distal dislocation of the hand brace and limits the flexor-extensor movements of the wrist.

These functions are capable of producing relief up to the complete control of the symptoms related to the carpal tunnel syndrome.

What is claimed is:

1. A hand brace for treatment of carpal tunnel syndrome comprising:

a prismatic-shaped cushion having a first face, a second face and a base therebetween defining a cuneiform cross section, a dorsal support having two ends, the dorsal support being connected to the prismatic-shaped cushion, the dorsal support being disposed on the back of the hand during use, the ends of the dorsal support being connected thereby forming a bandage embracing the metacarpal bones of the second and fifth fingers, a passage located between the cushion and the dorsal support, the cushion being wedged between the fingers of the band with the base distal from the palm of the hand, such that the palm sides of the third and fourth fingers slide through the passage and contact the cushion and the back sides of the second and fifth fingers contact the cushion such that the third and fourth fingers are maintained in an extended position, during use a removable wrist band, a strap connected to the wrist band and connected to the dorsal support, such that when worn, the hand brace simultaneously tightens the metacarpal bones and avoids distal dislocation of the hand brace and limits flexor-extension movements of the wrist during use.

2. The hand brace of claim 1, wherein the bandage is inelastic.

3. The hand brace of claim 1, wherein the bandage is elastic.

4. The hand brace of claim 1, wherein the strap is permanently connected to the dorsal support.

5. The hand brace of claim 1, wherein the strap is removably connected to the dorsal support.

6. The hand brace of claim 1, wherein the prismatic-shaped cushion has a first end and an opposite second end, the dorsal support being connected to the prismatic-shaped member by a first strip connected between the first end of the cushion and the dorsal support and a second strip connected between the second end of the cushion and the dorsal support.

* * * * *